US00PP19020P2

(12) United States Plant Patent
Klemm

(10) Patent No.: US PP19,020 P2
(45) Date of Patent: Jul. 15, 2008

(54) POINSETTIA PLANT NAMED 'NPCW06115'

(50) Latin Name: *Euphorbia pulcherrima*
Varietal Denomination: NPCW06115

(75) Inventor: Nils Klemm, Stuttgart (DE)

(73) Assignee: Klemm + Sohn GmbH + Co. KG, Stuttgart (DE)

( * ) Notice: Subject to any disclaimer, the term of this patent is extended or adjusted under 35 U.S.C. 154(b) by 0 days.

(21) Appl. No.: 11/728,152

(22) Filed: Mar. 23, 2007

(51) Int. Cl.
*A01H 5/00* (2006.01)

(52) U.S. Cl. ..... Plt./307
(58) Field of Classification Search ..... Plt./307
See application file for complete search history.

*Primary Examiner*—Annette H Para
(74) *Attorney, Agent, or Firm*—C. A. Whealy

(57) ABSTRACT

A new and distinct cultivar of Poinsettia plant named 'NPCW06115', characterized by its upright plant habit; freely branching habit; inflorescences with red-colored flower bracts; and good post-production longevity.

1 Drawing Sheet

Botanical designation: *Euphorbia pulcherrima.*
Cultivar denomination: 'NPCW06115'.

BACKGROUND OF THE INVENTION

The present invention relates to a new and distinct cultivar of Poinsettia plant, botanically known as *Euphorbia pulcherrima* Willd., and hereinafter referred to by the name 'NPCW06115'.

The new Poinsettia a product of a planned breeding program conducted by the Inventor in Stuttgart, Germany. The objective of the breeding program is to create new freely branching Poinsettia cultivars with attractive floral bract coloration and excellent post-production longevity.

The new Poinsettia originated from a cross-pollination made by the Inventor in 2000 of a proprietary selection of *Euphorbia pulcherrima* Willd. identified as code number T244, not patented, as the female, or seed, parent, with a proprietary selection of *Euphorbia pulcherrima* Willd. identified as code number T 126, not patented, as the male, or pollen, parent. The cultivar NPCW06115 was discovered and selected by the Inventor as a flowering plant within the progeny of the stated cross-pollination in a controlled environment in Stuttgart, Germany in 2002.

Asexual reproduction of the new Poinsettia by terminal vegetative cuttings in a controlled environment in Stuttgart, Germany since 2002, has shown that the unique features of this new Poinsettia are stable and reproduced true to type in successive generations of asexual reproduction.

SUMMARY OF THE INVENTION

The cultivar NPCW06115 has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'NPCW06115'. These characteristics in combination distinguish 'NPCW06115' as a new and distinct cultivar of Poinsettia:

1. Upright plant habit.
2. Freely branching habit.
3. Inflorescences with red-colored flower bracts.
4. Relatively large cyathia.
5. Good post-production longevity.

In side-by-side comparisons conducted in Stuttgart, Germany, plants of the new Poinsettia differed from plants of the female parent selection primarily in plant form as plants of the female parent selection were more upright than and not as broad as plants of the new Poinsettia.

In side-by-side comparisons conducted in Stuttgart, Germany, plants of the new Poinsettia differed from plants of the male parent selection in the following characteristics:

1. Plants of the new Poinsettia had darker green-colored leaves than plants of the male parent selection.
2. Plants of the new Poinsettia flowered earlier than plants of the male parent selection.
3. Plants of the new Poinsettia and the male parent selection differed in flower bract color as plants of the male parent selection had apricot-colored flower bracts.

Plants of the new Poinsettia can be compared to plants of the Poinsettia cultivar Primero, not patented. In side-by-side comparisons conducted in Stuttgart, Germany, plants of the new Poinsettia differed from plants of the cultivar Primero in the following characteristics:

1. Plants of the new Poinsettia were not as vigorous as plants of the cultivar Primero.
2. Plants of the new Poinsettia had thinner lateral branches than plants of the cultivar Primero.
3. Plants of the new Poinsettia had narrower flower bracts than plants of the cultivar Primero.
4. Plants of the new Poinsettia flowered earlier than plants of the cultivar Primero.
5. Plants of the new Poinsettia had fewer cyathia per inflorescence than plants of the cultivar Primero.

BRIEF DESCRIPTION OF THE PHOTOGRAPH

The accompanying photograph illustrates the overall appearance of the new Poinsettia. These photograph shows the colors as true as it is reasonably possible to obtain in colored reproductions of this type. Colors in the photograph may differ slightly from the color values cited in the detailed botanical description which accurately describe the colors of the new Poinsettia. The photograph comprises a top perspective view of a typical flowering plant of 'NPCW06115' grown in a container.

DETAILED BOTANICAL DESCRIPTION

In the following description, color references are made to The Royal Horticultural Society Colour Chart, 1995 Edition, except where general terms of ordinary dictionary significance are used. The aforementioned photograph and following observations and measurements describe plants grown in Stuttgart, Germany during the spring in a glass-covered greenhouse and under conditions and practices which approximate those generally used in commercial Poinsettia production. During the production of the plants, day temperatures ranged from 17° C. to 28° C., night temperatures ranged from 16° C. to 22° C. and light levels were maintained at or below 60 kilolux. Measurements and numerical values represent averages for typical flowering plants. Single plants were grown in 13-cm containers and were pinched one time. Plants were about four months old when the photograph and the detailed description were taken.

Botanical classification: *Euphorbia pulcherrima* cultivar NPCW06115.

Parentage:

*Female, or seed, parent.*—Proprietary selection of *Euphorbia pulcherrima* Willd. identified as code number T 244, not patented.

*Male, or pollen, parent.*—Proprietary selection of *Euphorbia pulcherrima* Willd. identified as code number T 126, not patented.

Propagation:

*Type.*—Terminal vegetative cuttings.

*Time to initiate roots, summer.*—About 12 days at 20° C.

*Time to initiate roots, winter.*—About 15 days at 20° C.

*Time to produce a rooted young plant, summer.*—About 20 days at 20° C.

*Time to produce a rooted young plant, winter.*—About 25 days at 20° C.

*Root description.*—Fibrous; white in color.

*Rooting habit.*—Freely branching; dense.

Plant description:

*Plant habit and form.*—Upright plant habit; inverted triangle. Inflorescences positioned above the foliar plane. Moderately vigorous growth habit.

*Plant height.*—About 25 cm to 30 cm.

*Plant diameter or spread.*—About 30 cm to 35 cm.

*Lateral branch description.*—Quantity: Freely branching habit, about five to seven lateral branches develop after pinching. Length: About 25 cm. Diameter: About 3 mm to 6 mm. Internode length: About 2 cm to 4 cm. Strength: Strong. Texture: Smooth, glabrous. Color: 143A overlain with 183A.

*Foliage description.*—Arrangement: Alternate, simple. Length: About 7 cm to 12 cm. Width: About 4 cm to 7 cm. Shape: Ovate. Apex: Acute. Base: Obtuse. Margin: Slightly lobed; slightly serrate. Venation pattern: Pinnate. Texture, upper and lower surfaces: Smooth, glabrous. Color: Developing foliage, upper surface: 144B. Developing foliage, lower surface: 143C. Fully expanded foliage, upper surface: 137B; venation, 138B. Fully expanded foliage, lower surface: 138B; venation, 138B. Petiole: Length: About 3 cm to 5 cm. Diameter: About 2 mm to 3 mm. Texture, upper and lower surfaces: Smooth, glabrous. Color, upper and lower surfaces: 183B.

Inflorescence description:

*Inflorescence type and habit.*—Inflorescences are compound corymbs of cyathia with colored flower bracts subtending the cyathia. One inflorescence per lateral branch. Flowers are not fragrant. Flowers persistent. Inflorescences positioned above the foliage.

*Natural flowering season.*—Early winter; inflorescence initiation and development is induced under long nyctoperiod conditions. Early flowering, response time is about 7.5 weeks.

*Post-production longevity.*—Good post-production longevity; plants of the new Poinsettia maintain good substance and bract color for about three to four weeks under interior conditions.

*Inflorescence size.*—Diameter: About 15 cm to 20 cm. Height (depth): About 2 cm to 4 cm.

*Flower bracts.*—Quantity per inflorescence: About seven to nine. Length: About 6 cm to 10 cm. Width: About 4 cm to 7 cm. Shape: Ovate. Apex: Acute. Base: Obtuse. Margin: Entire to slightly serrate. Texture, upper and lower surfaces: Smooth, glabrous. Venation pattern: Pinnate. Color: Developing or transitional bracts, upper and lower surfaces: 46B; venation, 46B. Developing or transitional bracts, upper and lower surfaces: 46B; venation, 46B. Bract petiole: Length: About 1 cm to 3 cm. Diameter: About 2 mm. Texture, upper and lower surfaces: Smooth, glabrous. Color, upper and lower surfaces: 187B.

*Cyathia.*—Quantity per corymb: About five to eight. Diameter of cyathia cluster: About 1 cm to 1.5 cm. Length: About 4 mm to 5 mm. Width: About 3 mm to 4 mm. Shape: Ovate. Color, immature and mature: 143C. Nectaries: Quantity per cyathium: About one or two. Size: About 2 mm to 3 mm. Color: Between 13A and 24A.

*Peduncles.*—Length: About 1 mm to 2 mm. Diameter: About 1 mm. Strength: Moderately strong. Texture: Smooth, glabrous. Color: 145A.

*Reproductive organs.*—Stamens: Quantity per cyathium: About five to ten. Anther shape: Ovate. Anther length: About 1 mm. Anther color: Between 9A and 12A. Amount of pollen: Moderate. Pollen color: Between 9A and 12A. Pistils: Quantity per cyathium: One. Pistil length: About 3 mm to 5 mm. Style length: About 2 mm to 3 mm. Style color: Close to 144B. Stigma shape: Two-parted. Stigma color: 185A. Ovary color: Close to 144A.

*Seed/fruit.*—Seed and fruit production has not been observed.

Disease/pest resistance: Plants of the new Poinsettia have not been shown to be resistant to pathogens and pests common to Poinsettias.

Temperature tolerance: Plants of the new Poinsettia have been observed to tolerate temperatures ranging from about 12° C. to about 35° C.

It is claimed:

1. A new and distinct Poinsettia plant named 'NPCW06115' as illustrated and described.

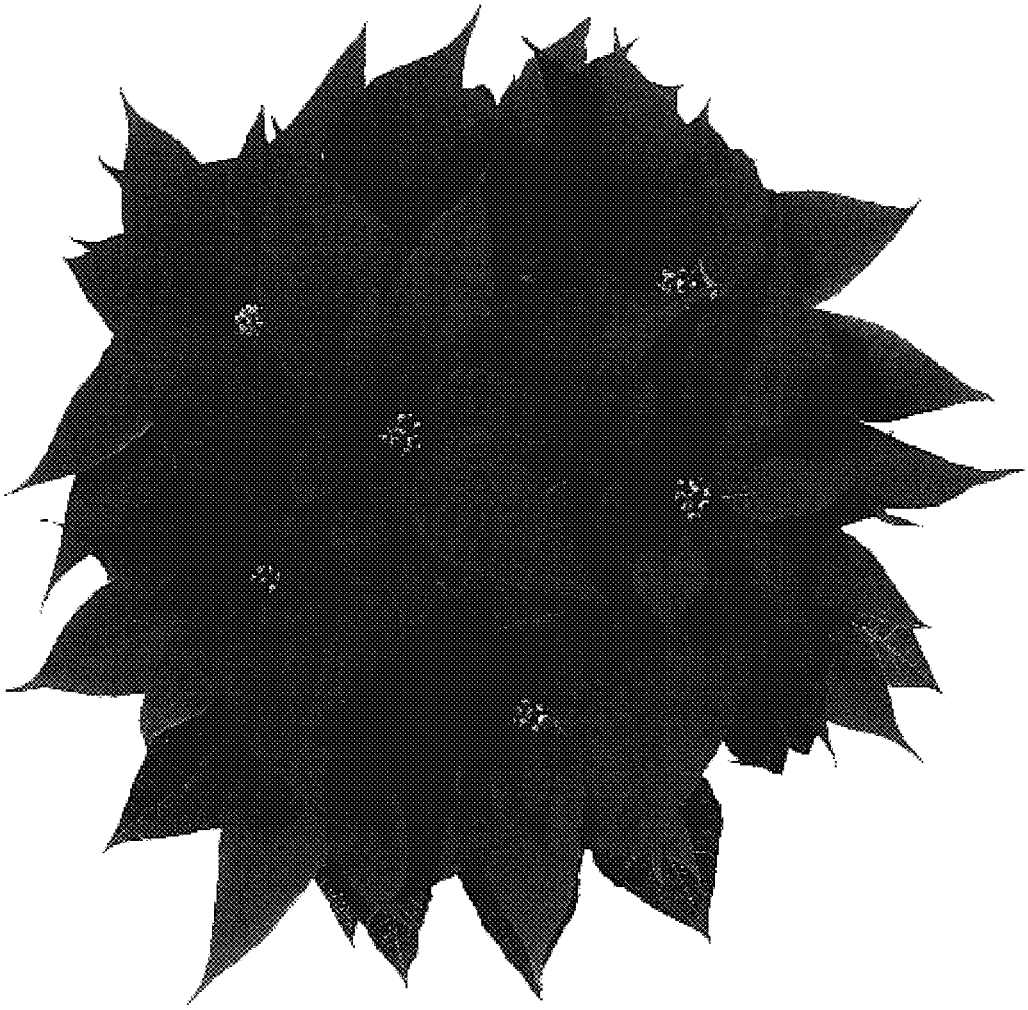

* * * * *